United States Patent
Limbert et al.

(10) Patent No.: US 9,159,216 B2
(45) Date of Patent: Oct. 13, 2015

(54) HAND HYGIENE DISPENSER MONITOR

(71) Applicant: DebMed USA LLC, Charlotte, NC (US)

(72) Inventors: Dean Philip Limbert, Derby (GB); Didier Bouton, Waterloo (CA); Paul Samuel Dodds, Ashbourne (GB); Christopher James Lang, Nottinghamshire (GB)

(73) Assignee: DEBMED USA LLC, Charlotte, NC (US)

( * ) Notice: Subject to any disclaimer, the term of this patent is extended or adjusted under 35 U.S.C. 154(b) by 0 days.

(21) Appl. No.: 13/765,856

(22) Filed: Feb. 13, 2013

(65) Prior Publication Data

US 2014/0225732 A1 Aug. 14, 2014

(51) Int. Cl.
*G08B 21/00* (2006.01)
*G08B 21/24* (2006.01)

(52) U.S. Cl.
CPC .................................. *G08B 21/245* (2013.01)

(58) Field of Classification Search
CPC ................................................... G08B 21/245
USPC ................. 340/540, 573.1, 539.11, 539.23
See application file for complete search history.

(56) References Cited

U.S. PATENT DOCUMENTS

| | | | | |
|---|---|---|---|---|
| 6,975,231 | B2* | 12/2005 | Lane et al. ................. | 340/573.1 |
| 7,898,407 | B2* | 3/2011 | Hufton et al. ............ | 340/539.11 |
| 8,237,558 | B2* | 8/2012 | Seyed Momen et al. ........................ | 340/539.11 |
| 8,395,515 | B2* | 3/2013 | Tokhtuev et al. ............. | 340/603 |
| 8,587,437 | B2* | 11/2013 | Kyle et al. ................... | 340/573.1 |
| 8,598,996 | B2* | 12/2013 | Wildman et al. ........ | 340/286.09 |
| 2007/0262259 | A1 | 11/2007 | Wu et al. | |
| 2009/0267776 | A1 | 10/2009 | Glenn et al. | |
| 2011/0148586 | A1 | 6/2011 | Anderson et al. | |
| 2011/0234407 | A1* | 9/2011 | Harris et al. ............... | 340/573.1 |
| 2012/0158419 | A1 | 6/2012 | Nuthi | |
| 2013/0187779 | A1* | 7/2013 | Pokrajac .................... | 340/573.1 |

FOREIGN PATENT DOCUMENTS

| | | |
|---|---|---|
| CA | 2783597 A1 | 1/2013 |
| WO | 2007090470 A1 | 8/2007 |

OTHER PUBLICATIONS

International Search Report and Written Opinion, Int'l Application No. PCT/IB2013/000646, Nov. 7, 2013, 11 pages.

\* cited by examiner

*Primary Examiner* — Toan N Pham
(74) *Attorney, Agent, or Firm* — McAndrews, Held & Malloy, Ltd.

(57) ABSTRACT

A monitor is located adjacent to a hand hygiene product dispenser and extends a sensor field adjacent to the hand hygiene product dispenser. The sensor senses activity adjacent to the hand hygiene product dispenser in the sensor field. The monitor determines whether sensed activity indicates a use of the hand hygiene product dispenser and reports a use of the dispenser to a monitoring system when a use is determined.

19 Claims, 12 Drawing Sheets

HAND HYGIENE DISPENSER MONITOR

RELATED APPLICATIONS

None.

FEDERALLY SPONSORED RESEARCH OR DEVELOPMENT

[Not Applicable]

MICROFICHE/COPYRIGHT REFERENCE

[Not Applicable]

FIELD

This disclosure relates to identifying and reporting hand hygiene events. Embodiments relate to a monitor that is located adjacent to a hand hygiene product dispenser. Embodiments relate to identifying use of a hand hygiene product dispenser.

BACKGROUND

Hand hygiene is essential for certain activities and services, including particularly healthcare and food preparation and service. The invention concerns identifying hand hygiene events by identifying use of hand hygiene dispensers.

For healthcare providers, the spread of healthcare acquired infections also known as HAI's has been an ever increasing challenge in healthcare facilities. HAIs can result from transmission of bacteria, viruses and other disease causing microorganisms from various sources such as a patient or environmental surfaces to another patient or surface via the hands of healthcare workers. Such transmission can result in an infection of a patient who was previously not infected. Health care facilities have battled MRSA (methicillin-resistant *staphylococcus aureus*) and VRSA (vancomycin-resistant *staphylococcus aureus*) and other drug resistant micro-organisms for many years. These problems have been more apparent in recent years. It is estimated that approximately 2,000,000 such HAIs occur annually in the U.S. alone resulting in about 100,000 deaths. The extra costs associated with these infections are estimated in the billions of dollars.

Healthcare institutions seek to prevent and control the spread of HAIs. One important aspect of such efforts is seeking to ensure that health care professionals comply with hand hygiene best practices. Hand hygiene can be accomplished by washing with soap and water and by using liquids such as a sanitizing product which does not require water or rinsing of the product. Hygiene products that are used for hand hygiene are commonly dispensed by dispensers that are located where hand hygiene is desired. Use of such dispensers indicates that hand hygiene has occurred. Dispensers have been adapted to report use such as those disclosed by U.S. patent application Ser. Nos. 12/823,475 and 13/427,467 which are assigned to the applicant of this application and incorporated herein by reference.

Hand hygiene is also recognized as essential in the food industry to prevent the spread of foodborne bacteria and/or viruses including Norovirus, the Hepatitis A virus, *Salmonella Typhi*, *Shigella* spp., and *Escherichia coli* (*E. coli*) O157:H7 or other Enterohemorrhagic or Shiga toxin-producing *E. coli*, *Staphylococcus aureus*, *Salmonella* spp. and *Streptococcus pyogenes*. Hand washing by food employees is essential after activities that contaminate hands and before activities during which pathogens may be spread to food.

BRIEF SUMMARY

An aspect of the present technology provides a sensor that is external to a hand hygiene product dispenser and that identifies actuations of the dispenser. Integration of the monitoring sensor into the internal workings of the dispenser is not required. Therefore a monitoring system including this sensor is not inherently tied to a specific dispenser or dispenser manufacturer. The present technology facilitates adoption of a monitoring system by avoiding the barrier to implementation of a monitoring system that is raised by the cost and effort of replacement of dispensing equipment and a potential change in hand hygiene product supplier.

In one aspect of the present technology, a sensor has sensor field that encompasses a region that is adjacent to a section of the dispenser where an object is present when the dispenser is actuated and dispenses a product.

An additional described aspect resides in providing a sensor from which a sensor field extends to a region adjacent to a hand hygiene product dispenser in which the presence of an object is highly indicative of use of the dispenser.

An additional described aspect resides in determining that a hand hygiene event has occurred based on a sensor indication of an object within a sensor field and communicating that occurrence to a system that monitors use of dispensers.

Yet an additional aspect of the present technology relates to a sensor that communicates with a monitoring system, that is positioned adjacent to a hand hygiene product dispenser and that is physically and functionally separate from the dispenser.

DESCRIPTION OF EMBODIMENTS

Embodiments described herein concern a monitor that indicates the presence of an object in a sensor field that is adjacent to a dispenser of a hand hygiene product dispenser. In particular, embodiments concern providing a sensor that is separate from the dispenser and that communicates with a system that monitors use of dispensers.

Embodiments will be described more fully hereinafter with reference to the accompanying drawings, in which embodiments are shown. Like reference numbers refer to like elements throughout. Other embodiments may, however, be in many different forms and are not limited to the embodiments set forth herein. Rather, these embodiments are examples. Rights based on this disclosure have the full scope indicated by the claims.

In facilities in which hand hygiene is important, hand hygiene products are stored and dispensed onto the hands from dispensers. Therefore, there is a direct correlation between dispenser usage and hand hygiene events. Dispenser usage data can provide the product volume used or the number of times the dispenser was used. Dispenser usage information can be collected manually or electronically. Electronically monitoring dispenser usage: 1) allows organization-wide trends to be tracked over time; 2) can be unobtrusive and designed to take up little additional space; 3) can be used across all shifts, twenty-four hours a day, and seven days a week; 4) requires minimal staff training; and 5) can be done in many different settings.

Figure 1:
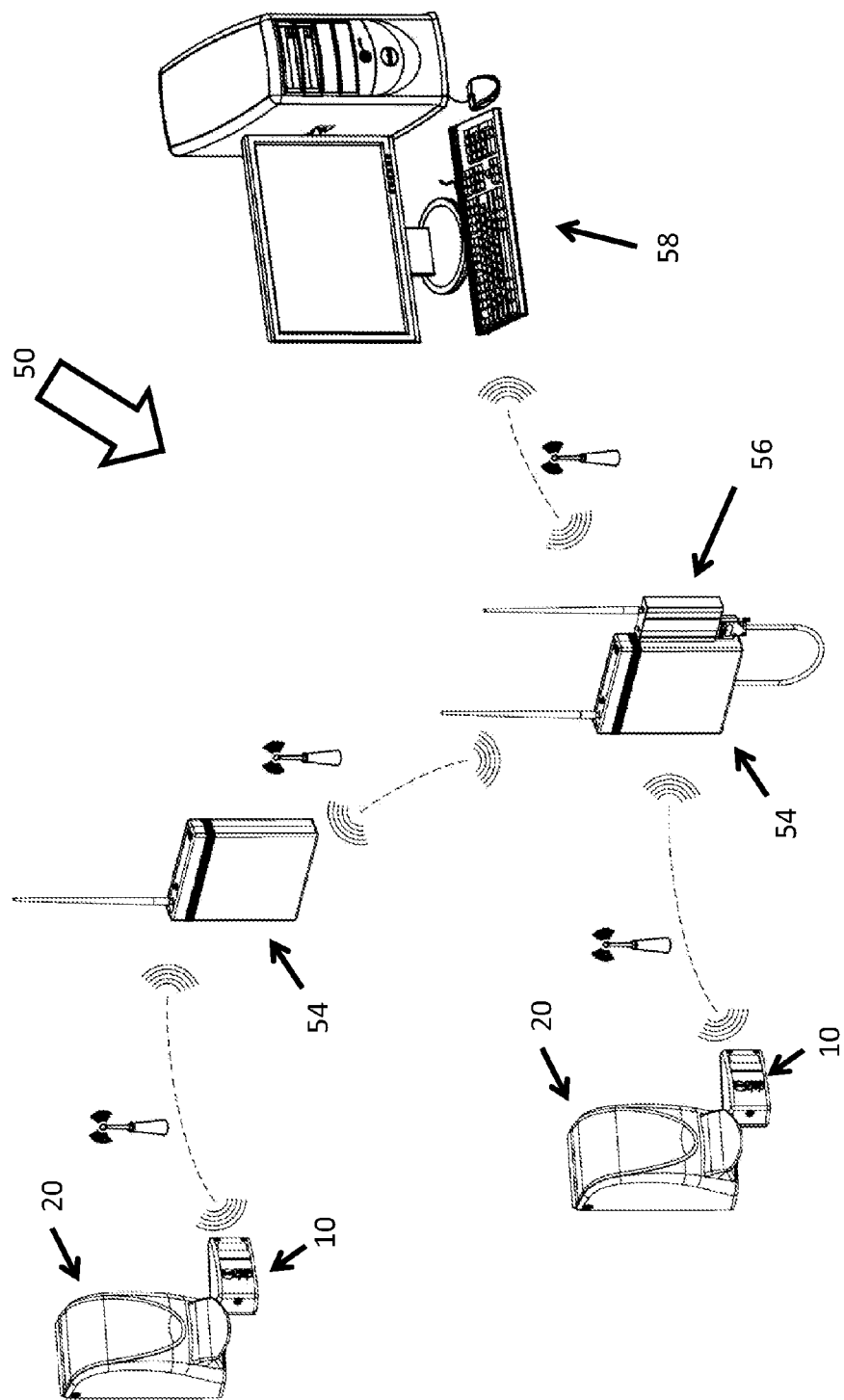
FIG. 1 is a diagram showing a wireless information collection system having dispenser use monitors in accordance with the present invention

FIG. 1 is a diagram showing a wireless information collection system in accordance with the present invention. System 50 is a dispenser usage monitoring system that comprises at least one dispenser 20, a wireless monitoring network, and a data collation server 58. A dispenser use monitor 10 is positioned adjacent to and associated with each dispenser 20. The monitor 10 identifies and reports use of a dispenser 20. The monitor 10 comprises a transmitter that wirelessly reports use of the associated dispenser 20 to the wireless monitoring system 50 that, in turn, forwards transmissions to the data collation server 58. The wireless monitoring system comprises at least one hub 54 and at least one gateway 56.

In the wireless system 50, the monitor 10 is wirelessly connected to a hub 54 and/or a gateway 56. The gateway 56 is connected to a data collation server 58. Data may be sent from the gateway 56 to the server 58 in a burst by way of a wired network (e.g., the internet) and/or any cellular network such as GSM. Collected data may also be sent to an offsite server for data processing.

Each dispenser use monitor 10 has a sensor therein and may be capable of storing data related to up to 100 or more dispenser activations. It will be appreciated by those skilled in the art that 100 activations is by way of example only and that typically each monitor may need to only store data relating to a few activations. This minimizes the chance of losing data in the event of queuing for receipt by the hub 54. The data is sent between the monitor 10 and the hub 54 and between the hub 54 and the gateway 56 in bursts which may be time or memory dependent.

Figure 2:
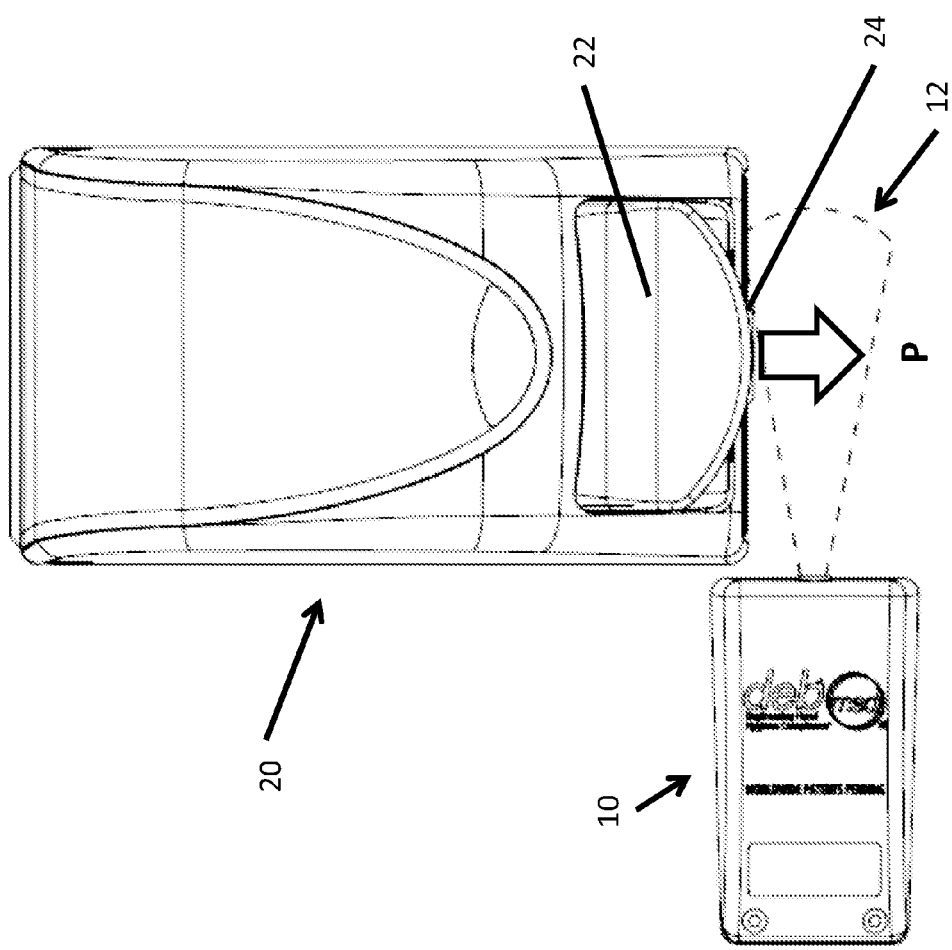
FIG. 2 is a front view of a dispenser use monitor positioned adjacent to a hand hygiene product dispenser.

FIG. 2 illustrates a monitor 10 positioned adjacent to a hand hygiene product dispenser 20 as also shown by FIG. 1. The dispenser 20 is depicted as mounted in a typical upright orientation. The dispenser 20 includes a lever 22 that is pressed from the front of the dispenser 20 to cause the dispenser 20 to dispense an amount of product P from a nozzle 24 at the lower portion of the dispenser 20 into a region adjacent to and below the nozzle 24 as indicated by the arrow adjacent to the nozzle 24. A user of the dispenser 20 places a hand beneath the nozzle 24 to receive a dispensed amount of hand hygiene product and operates the lever 22 either with a portion of the hand that receives the hand hygiene product or with the user's other hand.

A sensor field 12 extends from the monitor 10 into the region adjacent to the nozzle 24 at the lower portion of the dispenser 20. The monitor 10 is positioned to extend the sensor field 12 to encompass a region that is adjacent to and below the nozzle 24 into which hand hygiene product is dispensed. Preferably, that region includes the location at which a user of the dispenser 20 places his or her hand to receive a hand hygiene product dispensed from the nozzle 24 of the dispenser 20.

As shown by FIG. 2, the sensor field 12 extends in a direction that is generally perpendicular to the direction that hand hygiene product is dispensed from the nozzle 24. Because the sensor field 12 is adjacent to the nozzle 24, a user who operates the dispenser 20 using one hand to both operate the lever 22 and receive dispensed hand hygiene product will place that hand within the sensor field 12. Users who operate the dispenser 20 using one hand to operate the lever 22 and the other hand to receive dispensed hand hygiene product may not place the receiving hand within the sensor field 12. In order to extend the sensor field 12 farther along the path of dispensed product to encompass a hand that receives product at a location that is more separated from the dispenser 20, the monitor 10 may displaced downward from the dispenser 20 and\or may be oriented to extend the sensor field along a direction that crosses the path of dispensed product at an angle to also extend along the direction that product is dispensed from the dispenser 20.

Figure 3:
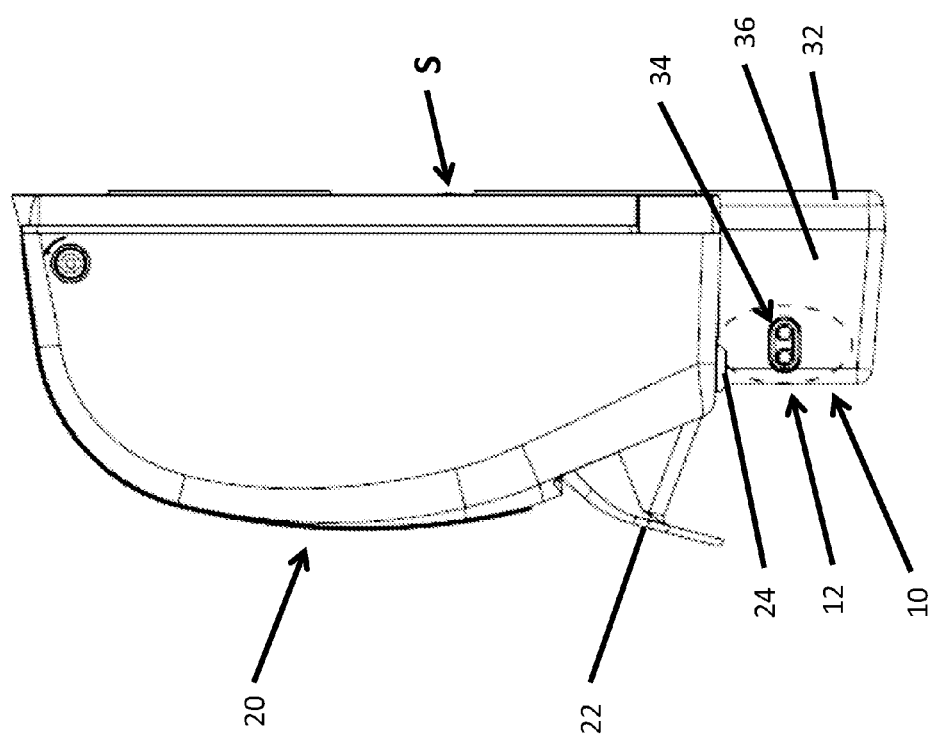
FIG. 3 is a side view of the monitor and dispenser of FIG. 2.

FIG. 3 illustrates a side view of the monitor 10 and the dispenser 20 showing the sensor field 12 adjacent to the nozzle 24. The dispenser 20 and the monitor 10 are mounted on the surface of a wall indicated as S on FIG. 3. The monitor 10 has a case 32. The sensor field 12 extends from the monitor 10 through an opening 34 in the side 36 of the case 32. The opening 34 is spaced from the surface S by approximately the same distance that the nozzle 24 is separated from the surface S. For conventional hand hygiene product dispensers, this distance is typically between 1½ inches and 5 inches, often between 1¾ inches and 2½ inches.

Figure 4:
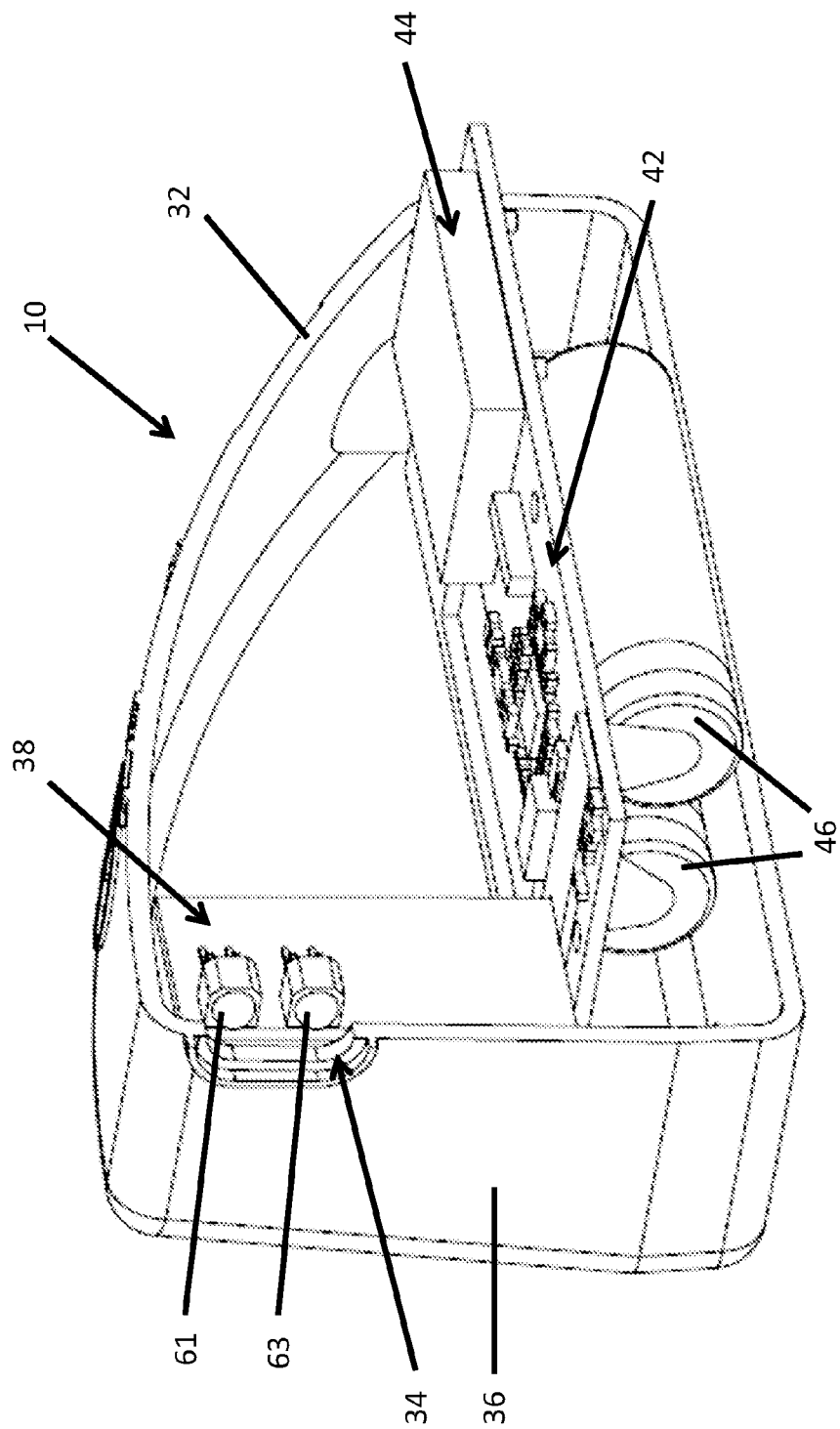
FIG. 4 is a cutaway view of the monitor of FIGS. 2 and 3.

FIG. 4 illustrates a cutaway view of the monitor 10. The case 32 of the monitor 10 encloses a proximity sensor 38, control and processing components 42, communication components 44 and batteries 46. The batteries 46 provide power to operate the proximity sensor 38, the control and processing components 42 and the communication components 44. The proximity sensor 38 is mounted adjacent to the opening 34 in the side 36 of the case 32.

The proximity sensor 38 includes an infrared emitter 61 and an infrared receiver 63 that are mounted adjacent to the opening 34. The emitter 61 emits infrared light through the opening 34. The emitter 61 is powered by the batteries 46 and controlled by the components 42. The infrared receiver 63 receives infrared light through the opening 34 and communicates with the components 42. The components 42 determine when an object is present near the opening 34 based on communication from the infrared receiver 63 when infrared light emitted by the emitter 61 is reflected to the infrared receiver 63. The region exterior to the monitor 10 adjacent to the opening 34 in which an object will reflect sufficient infrared light emitted by the emitter 61 to the receiver 63 to indicate the presence of the object is the sensor field 12 for the proximity sensor 38.

The control and processing components 42 may function to identify use of a dispenser and may determine that the presence of an object in the sensor field 12 does or does not indicate use of a dispenser for hand hygiene. An example of a detected object that does not indicate a hand hygiene event may be opening of a dispenser to replace a product cartridge within the dispenser. Such an event may be characterized by an object being present for a time that is longer than that of a hand hygiene event. Similarly, an object may pass through the sensor field and be present for a time that is shorter than a hand hygiene event. The control and processing components 42 may determine that such events are not hand hygiene events and not report those events to a monitoring system. As an example of such determination, multiple sensing of an object within a short time, for example 2 to 3 seconds, which may be multiple actuations of a dispenser for a single hand hygiene event rather than multiple users activating the dispenser very close together. Therefore, a plurality of activations within a predetermined activation period may be considered a single dispenser usage event. For example, a plurality of activations within a 1 to 4 second time frame may be considered a single dispenser usage event. For hand soaps and hand sanitizers, this may be set at 2.5 seconds. However, where dispenser usage is being monitored for different types of products in different types of facilities, this may be set for a different activation period.

The communication components 44 comprise an RF transceiver and antenna that wirelessly communicates with a monitoring system. The control and processing components 42 may include an embedded microprocessor and/or an embedded microcontroller and memory or other data storage components. The control and processing components 42 cause the communication components 44 to report determined use of the hand hygiene product dispenser to the monitoring system 50. The control and processing components 42 and the communication components 44 may function as the dispenser components that are described by U.S. application Ser. No. 13/427,467 which is assigned to the owner of this application, for reporting use of a dispenser to a monitoring system.

Figure 5:
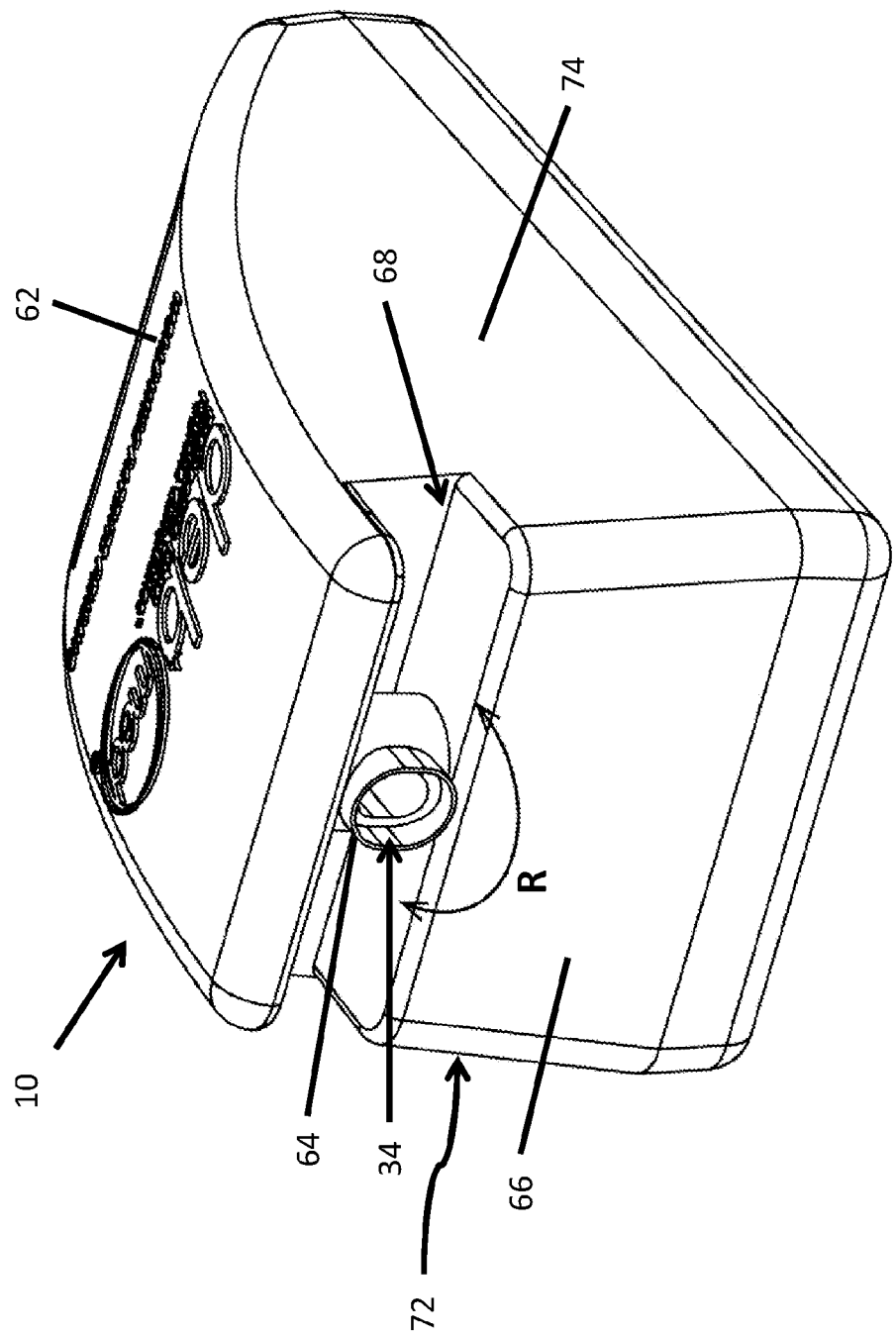
FIG. 5 is an oblique view of a monitor having a rotatable sensor mounting.

FIG. 5 illustrates a monitor 10 having a case 62. Similar to the case 32 of previously described embodiments, the case 62 encloses a proximity sensor 38, control and processing components 42, communication components 44 and batteries 46. The case 62 includes a side 66 that forms a channel 68 that extends toward the interior of the case 62 and across opposed sides 72 and 74 of the case 62. A rotatable sensor housing 64 is positioned within the channel 68 between the sides 72 and 74. The sensor housing 64 forms an opening 34 through which the proximity sensor 38 senses the presence of an object within the sensor field 12 of the monitor 10. The infrared emitter 61 and infrared receiver 63 may be mounted within the housing 64 and directed through the opening 34.

As indicated by arrow R in FIG. 5, the sensor housing 64 is mounted within the channel 68 to rotate to direct the opening 34 along the channel 68 toward either side 72 or side 74 or outwardly from the channel 68 along any direction between the directions to the sides 72 and 74. The rotatable sensor housing 64 thereby permits the sensor field 12 to be positioned to extend from the housing 62 along a selected direction outwardly from the side 66 of the monitor 10 between those directions toward sides 72 and 74.

Figure 6:
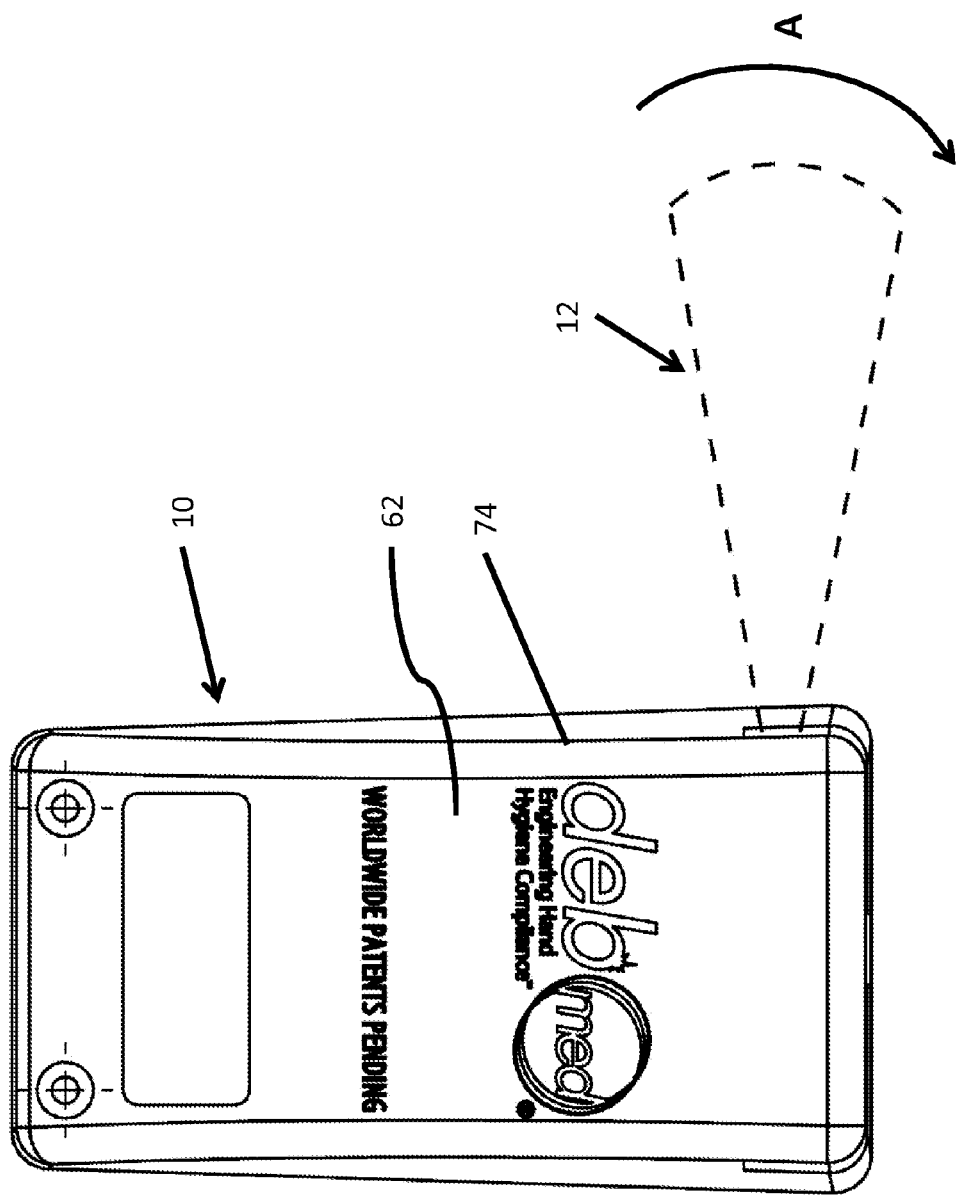
FIG. 6 is a front view of the monitor of FIG. 5.

FIG. 6 shows the monitor 10 having the case 62 with the housing 64 rotated to direct the sensor field 12 outwardly from the side 74 of the case 62. The monitor 10 having the case 62 and the housing 64 directed as in FIG. 6 can be positioned in the vertical orientation illustrated by FIG. 6 adjacent to a vertically oriented dispenser 20 as shown by FIG. 2. A monitor 10 positioned in that orientation need not extend downwardly as far as the monitor 10 oriented as depicted by FIG. 2. Similarly, the monitor 10 oriented as depicted by FIG. 6 need not extend as far from the dispenser 20 as that shown by FIG. 2. Further, as indicated by the arrow A in FIG. 6, the housing 64 may be rotated to extend the sensor field 12 at an angle that is at a downward angle across the path of dispensed product as described above.

Figure 7:
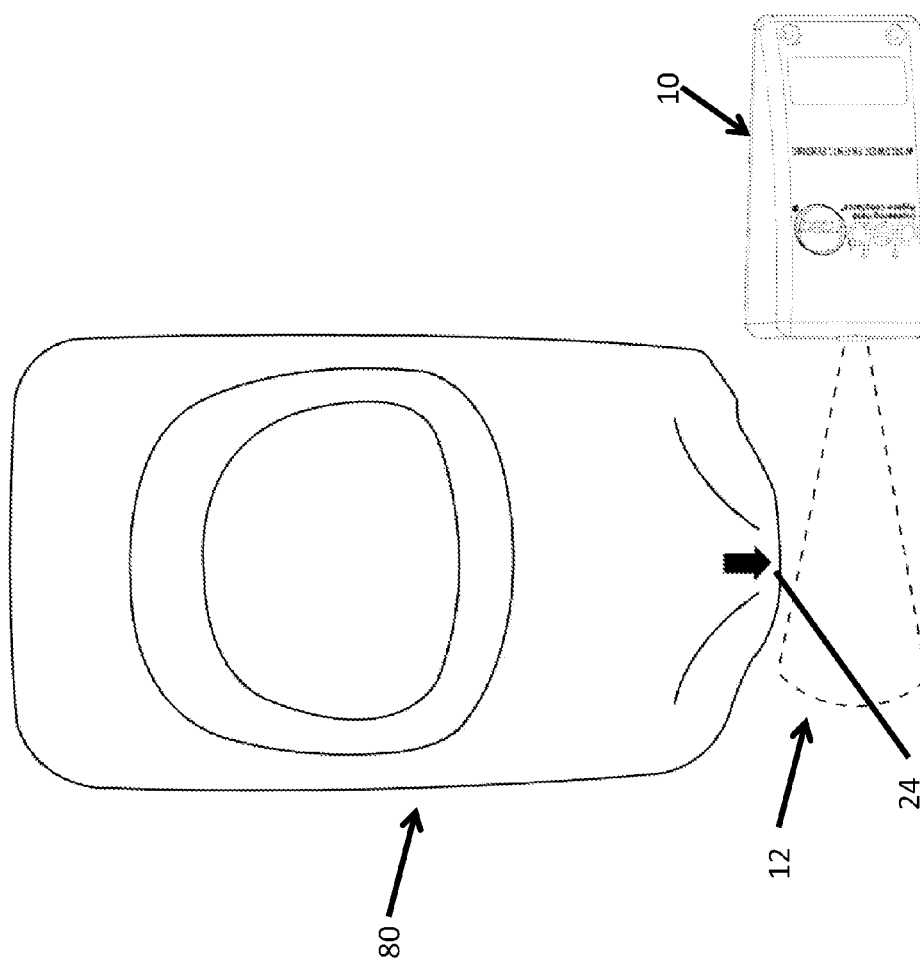
FIG. 7 is a front view of a monitor positioned adjacent to a touch-free hand hygiene product dispenser.

The monitor 10 may have a proximity sensor that does not interfere with and is not interfered with by a proximity sensor of a touch free dispenser. FIG. 7 illustrates a monitor 10 positioned adjacent to a touch-free dispenser 80. The touch-free dispenser 80 has a nozzle 24 that dispenses product when an object is positioned below the nozzle 24. The monitor 10 may have an infrared proximity sensor as described above that functions with the touch-free dispenser 80 that uses an infrared sensor to actuate dispensing of a product. The monitor 10 may have the case 62 with the rotatable sensor housing 64 so that the sensor field 12 may be positioned to include the location at which a hand will activate dispensing of product by the touch free sensor 80.

Figure 8:
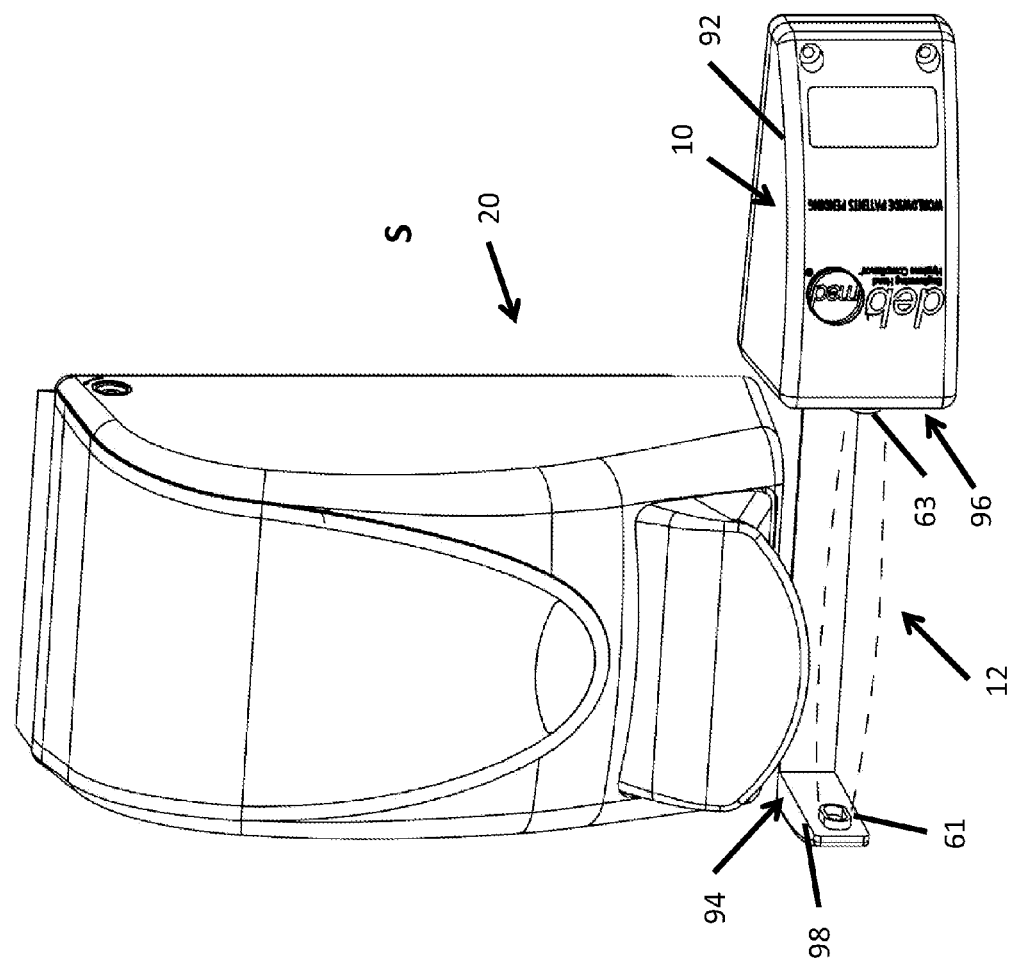
FIG. 8 is an oblique view of a sensor positioned to extend beneath a hand hygiene product dispenser.

FIG. 8 shows the monitor 10 having a case 92 positioned adjacent to and below a dispenser 20. An extension 94 extends from a side 96 of the case 92 below the dispenser 20 and along a surface S on which the monitor 10 and the dispenser 20 are mounted. The extension 94 forms a leg 98 that extends away from the surface S at a location that is separated from the case 92 so that the dispenser 20 dispenses hand hygiene product at a location that is between the leg 98 and the surface 96 of the case 92. An infrared emitter 61 is mounted to the leg 98 to direct infrared light toward a receiver 63 at the surface 96 of the case 92. The sensor field 12 extends from the emitter 61 to the receiver 63.

The proximity sensor of the monitor 10 that senses the presence of an object need not be based on infrared light. The proximity sensor may be an RF proximity sensor or a capacitive proximity sensor. Other sensors that may also be used include ultrasonic sensors (sonar), reflective photocell sensors, optical sensors and low power laser based sensors.

Monitors may identify activation of a dispenser based on activity adjacent to a dispenser other than presence of an object adjacent to the dispenser. Monitors described above identify activation of a dispenser based on proximity sensors sensing the presence of an object adjacent to a dispenser. The presence of the object, and in some cases the duration of its presence, represent activity adjacent to the dispenser from which dispenser use may be identified. As discussed for embodiments described below, a monitor may use one or more sensors to determine motion adjacent to a dispenser and identify activation of a dispenser identified based on motion adjacent to a dispenser.

The sensor field 12 need not encompass the region into which a dispenser dispenses a product. The sensor field 12 may instead encompass a region that is occupied during dispensing of a product such as a region adjacent to a lever that causes the dispenser to dispense a product.

Figure 9:
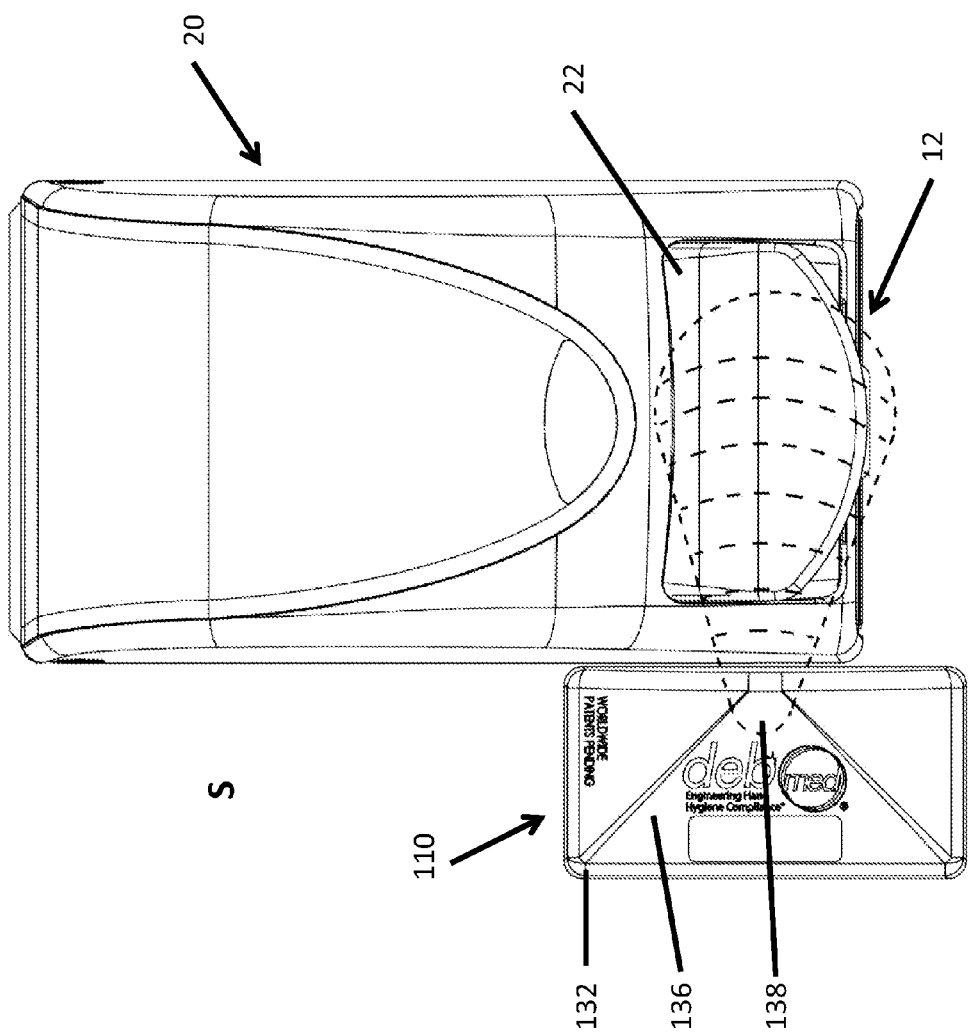
FIG. 9 is front view of a hand hygiene product dispenser and a monitor positioned adjacent to an actuating lever of the dispenser.
Figure 10:
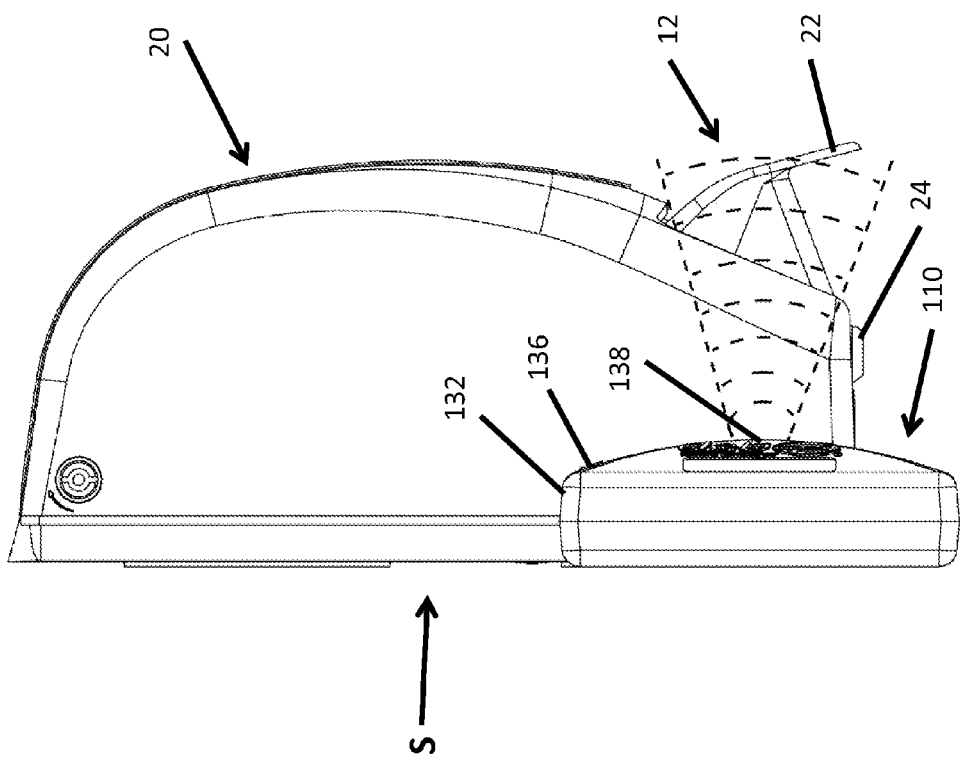
FIG. 10 is side view of a hand hygiene product dispenser and a sensor shown by FIG. 9.

FIGS. 9 and 10 illustrates a monitor 110 positioned adjacent to a hand hygiene product dispenser 20 mounted to a surface S. As described above, the dispenser 20 includes a lever 22 that is pressed from the front of the dispenser 20 to cause the dispenser 20 to dispense an amount of from a nozzle 24 at the lower portion of the dispenser 20. The monitor 110 is positioned to extend the sensor field 12 to encompass a region that includes the lever 22 at the front of the lower portion of the dispenser 20. The sensor field 12 includes at least a portion of the region into which a user's hand is positioned to operate the lever 22 to dispense hand hygiene product from the dispenser 20.

FIG. 10 illustrates a side view of the monitor 110 and the dispenser 20 showing the sensor field 12 extending to the lever 22. The dispenser 20 and the monitor 110 are mounted on the surface of a wall indicated as S on FIG. 10. The monitor 110 has a case 132. An ultrasonic proximity sensor 138 is positioned on a side 136 of the case 132 that faces away from the surface S. The ultrasonic proximity sensor 138 emits sensor waves to form the sensor field 12 and receives wave reflection from objects within that field. In addition to identifying the presence of an object (user's hand) with the sensor field 12, the monitor 110 can determine the direction of movement of an object within the sensor field 12. The monitor 110 determines the timing of reflected sensor waves and based on those timings ascertains whether the users hand and the lever 22 are travelling towards or away from the dispenser 20. Based on this determination, the monitor 110 identifies hand hygiene use of the dispenser 20 based on identified travel of an object in the sensor field. The monitor 110 reports identified use of the dispenser 20 to a hand hygiene monitoring system.

An advantage of provided by a monitors such as 110 that can determine direction of movement hand operating a dispenser 20 is that the number of lever actuations may be identified. A dispenser actuation causes the dispenser 20 to dispense a known amount of hand hygiene product. Identifying the number of actuations can identify use patterns of the dispenser so that the amount of hand hygiene product actually dispensed from the dispenser both for individual hand hygiene uses (number of actuations per use) and the total product usage may be determined. Total product dispensed can be used to schedule refilling of a dispenser.

Figure 11:
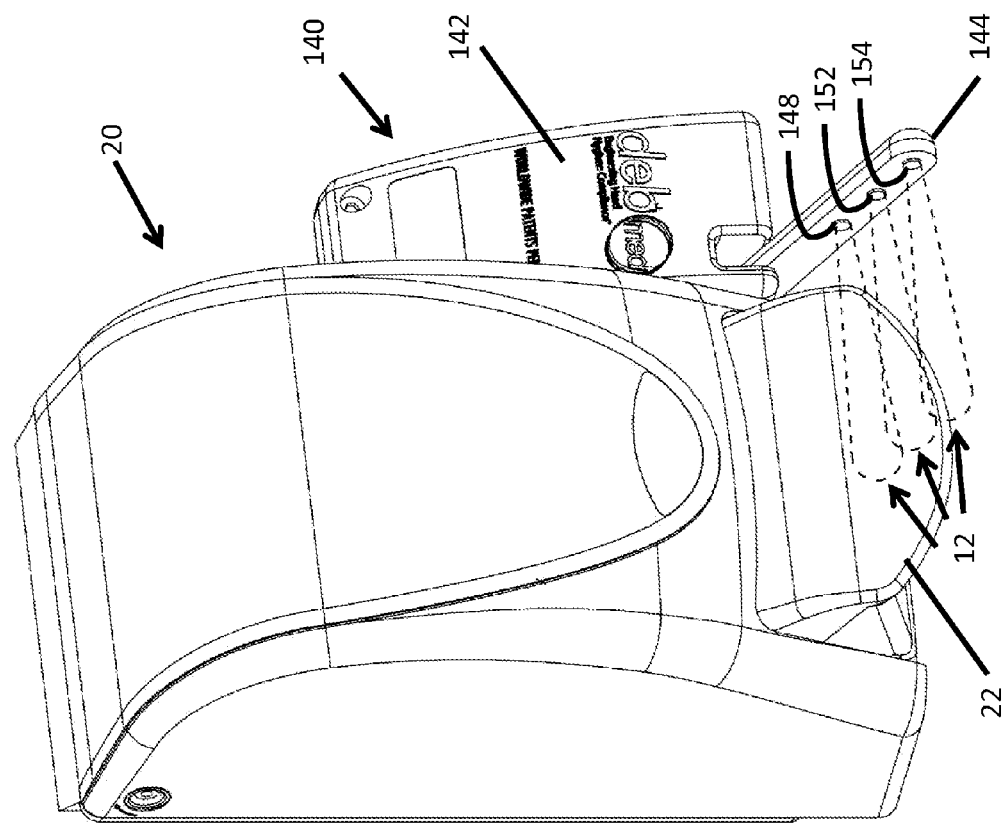
FIG. 11 is an oblique view of a hand hygiene product dispenser and a monitor.
Figure 12:
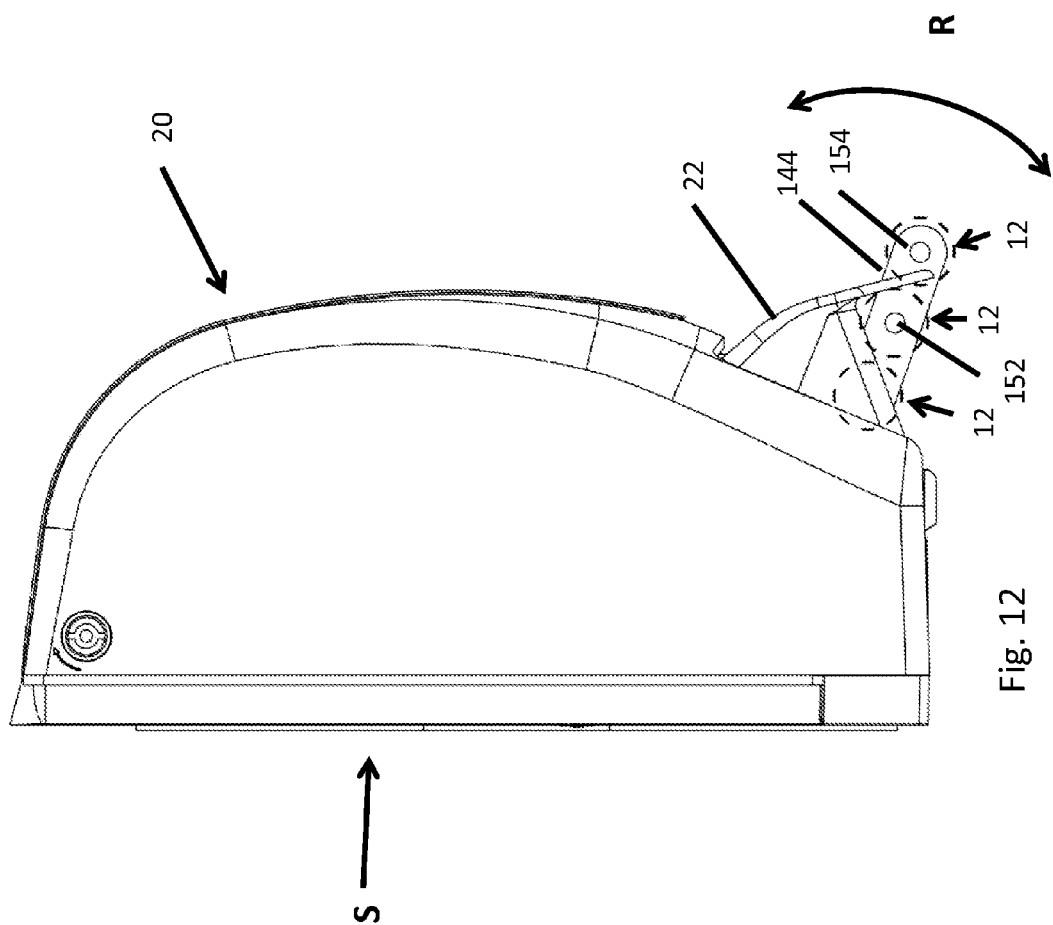
FIG. 12 is a side view of the hand hygiene product dispenser and monitor of FIG. 11.

FIGS. 11 and 12 illustrate a monitor 140 positioned adjacent to a hand hygiene product dispenser 20. The monitor 140 and the dispenser 20 are mounted to a surface S. As described above, a lever 22 extends from the dispenser 20. The lever 22 is pressed from the front of the dispenser 20 toward the surface S to cause the dispenser 20 to dispense an amount of hand hygiene product from a nozzle 24 at the lower portion of the dispenser 20. The monitor 140 includes a case 142. A sensor arm 144 extends from the case 142 and generally away from the surface S. The sensor arm 144 is adjacent to the lever 22 of the dispenser 20 and extends beyond the lever 22. Capacitive proximity sensors 148, 152 and 154 are mounted to the sensor arm 144. A sensor field 12 extends from each of sensors 148, 152 and 154 generally perpendicular to the sensor arm 144. As best shown by FIG. 12, the sensor field 12 of the sensor 148 is adjacent to the dispenser 20. The sensor field 12 from the sensor 152 is adjacent the sensor field 12 from the sensor 148 and farther from the dispenser 20 than the sensor field 12 of the sensor 148. The sensor field 12 from the sensor 154 is adjacent the sensor field 12 from the sensor 152 and farther from dispenser 20 than the sensor field 12 of the sensor 152. The sensor field 12 from the sensor 154 encompasses a portion of the lever 22 when, as shown by FIG. 12, the lever is extended from the dispenser 20. The sensor fields 12 are approximately parallel to each other and extend adjacent to the dispenser 20. When the dispenser 20 is used by a user, the lever 22 is pressed by the user to cause the lever 22 to move toward the dispenser 20. During that use, the lever 22 and the user's hand move through the sensor fields 12.

The sensors 148, 152 and 154 can individually sense an object in the sensor field 12 that extends from the sensor. The monitor 140 can identify movement of an object, including the lever 22, toward and away from the dispenser 20 based on sequential sensing of an object by the sensors 148, 152 and 154. The monitor 140 can thereby function as described for the monitor 110 to identify direction of movement of a hand operating the lever 22 of the dispenser 20. A number of sensors other than three may be positioned along the arm 144. The minimum number for identifying direction of movement is two. A greater number may be used limited by sensor size and space constraints adjacent to the dispenser 20. Sensors mounted to the arm 144 may be identical sensors. Other types of sensors and different sensors in combinations could also be used.

As indicated by arrow R in FIG. 12, the sensor arm 144 is mounted to the housing 142 to rotate. Rotation of the arm 144 will position the sensors 148, 152 and 154 at desired locations adjacent to the dispenser 20. Further, the monitor 140 could be positioned on the opposite side of the dispenser 20 by rotating the monitor 180 degrees on the surface S to direct the sensor fields oppositely from the direction shown by FIGS. 11 and 12.

The present invention is not limited to embodiments described herein. By way of example, the communication from the sensor to a monitoring system need not be wireless communication. The sensor may communicate with a monitoring system by other means including wired connections and optical communication. Other sensors and criteria for determining use of a dispenser may also be used in accordance with the invention. In addition, the proximity sensor may be movable on the sensor other than as described. The sensor may be mounted to translate to move the proximity sensor and thereby the sensor field along one or more directions.

The invention claimed is:

1. A monitor for augmenting a hand hygiene product dispenser that is mounted to a wall, the monitor comprising:
   a case that is separate from the hand hygiene product dispenser and configured to be mounted to the wall adjacent to the hand hygiene product dispenser;
   a sensor that is mounted to the case and that is configured to extend a sensor field from the wall-mounted case to a region adjacent to a product-dispensing nozzle of a hand hygiene product;
   processing components that receive communications from the sensor and that determine whether the communications from the sensor indicate use of the hand hygiene product dispenser;
   communication components connected to the processing components, the communication components configured to report determined use of the hand hygiene product dispenser to a monitoring system; and an extension configured to extend from a side of the case and along the wall to which the case and hand hygiene product dispenser are mounted;
   wherein the extension comprises a leg that extends away from the wall at a location separate from the case such that the product-dispensing nozzle dispenses hand hygiene products at a location between the leg and the side of the case;
   wherein the sensor comprises an infrared transmitter mounted to the leg and an infrared receiver at the side of the case;
   wherein the infrared receiver communicates to the processing components when infrared light emitted by the infrared transmitter is reflected to the infrared receiver; and
   wherein the processing components determine whether an object is present in the sensor field based on receipt of the infrared light by the infrared receiver.

2. The monitor of claim 1, wherein the communication components comprise an RF transceiver for wireless communication.

3. A monitor for augmenting a hand hygiene product dispenser that is mounted to a wall, the monitor comprising:
   a case that is separate from the hand hygiene product dispenser and configured to be mounted to the wall adjacent to the hand hygiene product dispenser;

a sensor that is mounted to the case and that is configured to extend a sensor field from the wall-mounted case to a region adjacent to a product-dispensing nozzle of a hand hygiene product;

processing components that receive communications from the sensor and that determine whether the communications from the sensor indicate use of the hand hygiene product dispenser; communication components connected to the processing components, the communication components configured to report determined use of the hand hygiene product dispenser to a monitoring system;

wherein the sensor comprises an ultrasonic sensor mounted to a side of the case and positioned to detect waves associated with an object moving in the sensor field;

wherein the ultrasonic sensor communicates to the processing components when waves are reflected to the ultrasonic sensor; and wherein the processing components determine whether the object is moving in the sensor field based on communication from the ultrasonic sensor.

4. The monitor of claim 3, wherein the sensor is rotatably mounted to the case and rotation of the sensor changes the direction of the sensor field.

5. The monitor of claim 3, wherein the communication components comprise an RF transceiver for wireless communication.

6. A monitor for augmenting a hand hygiene product dispenser that is mounted to a wall, the monitor comprising:

a case that is separate from the hand hygiene product dispenser and configured to be mounted to the wall adjacent to the hand hygiene product dispenser;

a sensor that is mounted to the case and that is configured to extend a sensor field from the wall-mounted case to a region adjacent to a product-dispensing nozzle of a hand hygiene product;

processing components that receive communications from the sensor and that determine whether the communications from the sensor indicate use of the hand hygiene product dispenser; and communication components connected to the processing components, the communication components configured to report determined use of the hand hygiene product dispenser to a monitoring system;

wherein the sensor comprises a sensor arm that extends from the case and away from the wall, and a plurality of proximity sensors positioned along the sensor arm and adjacent to each other;

wherein each proximity sensor generates a sensor field perpendicular to the sensor arm into a region proximate a lever of the hand hygiene product dispenser such that the lever sequentially passes through the generated sensor fields of the plurality of proximity sensors when depressed;

wherein the proximity sensors each communicate to the processing components when an object is sensed by the proximity sensor; and wherein the processing components infers movement of the lever based on communications from the proximity sensors.

7. The monitor of claim 6, wherein the plurality of proximity sensors comprises three proximity sensors at separated locations along the sensor arm.

8. The monitor of claim 6, wherein the communication components comprise an RF transceiver for wireless communication.

9. A monitor for augmenting a hand hygiene product dispenser that is mounted to a wall, the monitor comprising:

a case that is separate from the hand hygiene product dispenser and configured to be mounted to the wall adjacent to the hand hygiene product dispenser;

a sensor that is mounted to the case and that is configured to extend a sensor field from the wall-mounted case to a region adjacent to a product-dispensing nozzle of a hand hygiene product;

processing components that receive communications from the sensor and that determine whether the communications from the sensor indicate use of the hand hygiene product dispenser;

communication components connected to the processing components, the communication components configured to report determined use of the hand hygiene product dispenser to a monitoring system; and an extension configured to extend from a side of the case and along the wall to which the case and hand hygiene product dispenser are mounted;

wherein the extension comprises a leg that extends away from the wall at a location separate from the case such that the product-dispensing nozzle dispenses hand hygiene products at a location between the leg and the side of the case;

wherein the sensor comprises an infrared transmitter mounted to the leg and an infrared receiver at the side of the case;

wherein the infrared transmitter and receiver develop the sensor field that extends to the region adjacent the product-dispensing nozzle; and wherein the infrared receiver creates an indication of a presence of an object in the sensor field when infrared light emitted by the infrared transmitter is blocked from reaching the infrared receiver.

10. The monitor of claim 9, wherein the communication components comprise an RF transceiver for wireless communication.

11. A method of augmenting a hand hygiene product dispenser that is mounted to a wall, the method comprising:

mounting a separate, external monitor to the wall such that a sensor field of the monitor extends into a region associated with a product-dispensing nozzle of the hand hygiene product dispenser;

sensing, with the separate, external monitor, activity in the sensor field;

determining, with the separate, external monitor, whether the sensed activity indicates use of the hand hygiene product dispenser;

communicating, from the separate, external monitor to a monitoring system, an indication that the hand hygiene product dispenser has been used;

developing at least another sensor field that extends into another region adjacent to the product-dispensing nozzle; and sensing sequential activity in the two or more sensor fields;

wherein said determining whether the sensed activity indicates use of the dispenser is based on the sensed sequential activity in the two or more sensor fields.

12. The method of claim 11, wherein said sensing activity in the sensor field comprises sensing presence of an object in the sensor field.

13. The method of claim 11, wherein said sensing activity in the sensor field comprises sensing motion of an object in the sensor field.

14. The method of claim 11, wherein said sensing activity in the sensor field comprises sensing movement of a lever of the hand hygiene dispenser that causes the hand hygiene dispenser to dispense an amount of a hand hygiene product.

15. The method of claim 11, wherein said sensing activity in the sensor field comprises sensing an object actuating a lever of the hand hygiene dispenser to cause the hand hygiene product dispenser to dispense a hand hygiene product.

16. The method of claim 11, wherein said communicating comprises wirelessly transmitting the indication to the monitoring system.

17. The method of claim 11, wherein: said sensing activity in the sensor field comprises sensing a presence of an object in the sensor field; and said determining comprises determining, based on a length of time that the object is present in the sensor field, whether the hand hygiene product dispenser has been used.

18. A monitor for augmenting a hand hygiene product dispenser that is mounted to a wall, the monitor comprising:
- a case that is separate from the hand hygiene product dispenser and configured to be mounted to the wall adjacent to the hand hygiene product dispenser;
- a sensor that is mounted to the case and that is configured to extend a sensor field from the wall-mounted case to a region adjacent to a product-dispensing nozzle of a hand hygiene product;
- processing components that receive communications from the sensor and that determine whether the communications from the sensor indicate use of the hand hygiene product dispenser; and
- communication components connected to the processing components, the communication components configured to report determined use of the hand hygiene product dispenser to a monitoring system; and
- wherein the sensor extends a second sensor field to another region adjacent to the product-dispensing nozzle; and
- wherein the processing components further determine whether the communications from the sensor indicates use of the hand hygiene product dispenser based on sensed sequential activity of the sensor field and the second sensor field.

19. The monitor of claim 18, wherein the communication components comprise an RF transceiver for wireless communication.

* * * * *